US008996098B2

(12) United States Patent
Spector

(10) Patent No.: US 8,996,098 B2
(45) Date of Patent: *Mar. 31, 2015

(54) SYSTEM AND METHOD FOR DIAGNOSING AND TREATING DISEASE

(71) Applicant: Donald Spector, New York, NY (US)

(72) Inventor: Donald Spector, New York, NY (US)

(*) Notice: Subject to any disclaimer, the term of this patent is extended or adjusted under 35 U.S.C. 154(b) by 7 days.

This patent is subject to a terminal disclaimer.

(21) Appl. No.: 14/025,361

(22) Filed: Sep. 12, 2013

(65) Prior Publication Data

US 2014/0039323 A1 Feb. 6, 2014

Related U.S. Application Data

(63) Continuation-in-part of application No. 13/529,191, filed on Jun. 21, 2012, which is a continuation-in-part of application No. 13/438,003, filed on Apr. 3, 2012.

(60) Provisional application No. 61/612,575, filed on Mar. 19, 2012, provisional application No. 61/650,401, filed on May 22, 2012, provisional application No. 61/650,429, filed on May 22, 2012, provisional application No. 61/700,350, filed on Sep. 13, 2012.

(51) Int. Cl.
A61B 1/04 (2006.01)
A61B 5/06 (2006.01)
(Continued)

(52) U.S. Cl.
CPC ........... *A61B 1/00009* (2013.01); *A61B 5/0084* (2013.01); *A61B 1/04* (2013.01); *A61B 1/0676* (2013.01); *A61B 5/4836* (2013.01); *A61B 1/00087* (2013.01); *A61N 5/0603* (2013.01); *A61B 5/745* (2013.01); *A61B 10/04* (2013.01); *G06F 19/321* (2013.01); *A61B 5/0077* (2013.01); *A61N 5/0601* (2013.01); *A61N 5/0624* (2013.01); *A61B 1/0005* (2013.01); *A61B 1/00055* (2013.01); *A61B 6/461* (2013.01); *A61B 1/043* (2013.01); *A61B 6/5217* (2013.01); *A61B 6/563* (2013.01); *A61B 5/055* (2013.01); *G06F 19/345* (2013.01)
USPC .......................................... 600/476; 600/104

(58) Field of Classification Search
CPC ... A61B 1/0008; A61B 1/00087; A61B 10/04
See application file for complete search history.

(56) References Cited

U.S. PATENT DOCUMENTS 5,911,139 A 6/1999 Jain et al.
6,224,542 B1 5/2001 Chang et al.
(Continued)

FOREIGN PATENT DOCUMENTS

JP 2006-208857 A 8/2006

Primary Examiner — Long V Le
Assistant Examiner — Angela M Hoffa
(74) Attorney, Agent, or Firm — Collard & Roe, P.C.

(57) ABSTRACT

A method and system for diagnosing and treating infection or disease, in which an individual takes a photograph of an infected or diseased area of a body using a camera connected to a microprocessor. The photograph is sent to a diagnosing center having a server with a second microprocessor and a database of photographs correlated with different diseases and infections. The second microprocessor scans the image received from the camera and compares it to the photographs in the database. If a match is found, the second microprocessor then notes the disease or bacteria corresponding to the matching photograph. The second microprocessor then searches an additional database correlated to the match, to further refine the diagnosis. The second microprocessor then searches the second database for a treatment corresponding to the identified disease or bacteria. Once a treatment is identified, information regarding this treatment is automatically sent to the individual's microprocessor.

9 Claims, 7 Drawing Sheets

(51) Int. Cl.
*A61B 1/00* (2006.01)
*A61B 5/00* (2006.01)
*A61B 1/06* (2006.01)
*A61N 5/06* (2006.01)
*A61B 10/04* (2006.01)
*G06F 19/00* (2011.01)
*A61B 6/00* (2006.01)
*A61B 5/055* (2006.01)

(56) References Cited

U.S. PATENT DOCUMENTS

| | | | |
|---|---|---|---|
| 6,782,137 B1 | 8/2004 | Avinash | |
| 7,706,626 B2 | 4/2010 | Heath et al. | |
| 7,756,309 B2 | 7/2010 | Gholap et al. | |
| 7,760,927 B2 | 7/2010 | Gholap et al. | |
| 8,049,814 B2 | 11/2011 | Leibler et al. | |
| 8,202,214 B2* | 6/2012 | Doguchi et al. | 600/168 |
| 8,840,566 B2* | 9/2014 | Seibel et al. | 600/566 |
| 2007/0015989 A1 | 1/2007 | Desai et al. | |
| 2011/0009163 A1 | 1/2011 | Fletcher et al. | |
| 2012/0314049 A1 | 12/2012 | Gu et al. | |
| 2013/0016963 A1 | 1/2013 | Miller | |
| 2013/0245417 A1* | 9/2013 | Spector | 600/407 |
| 2013/0245458 A1* | 9/2013 | Spector | 600/476 |

* cited by examiner

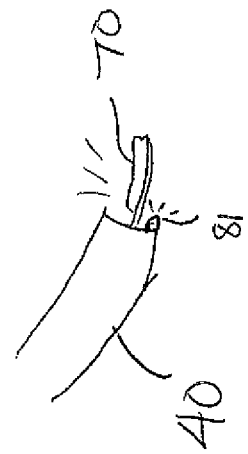
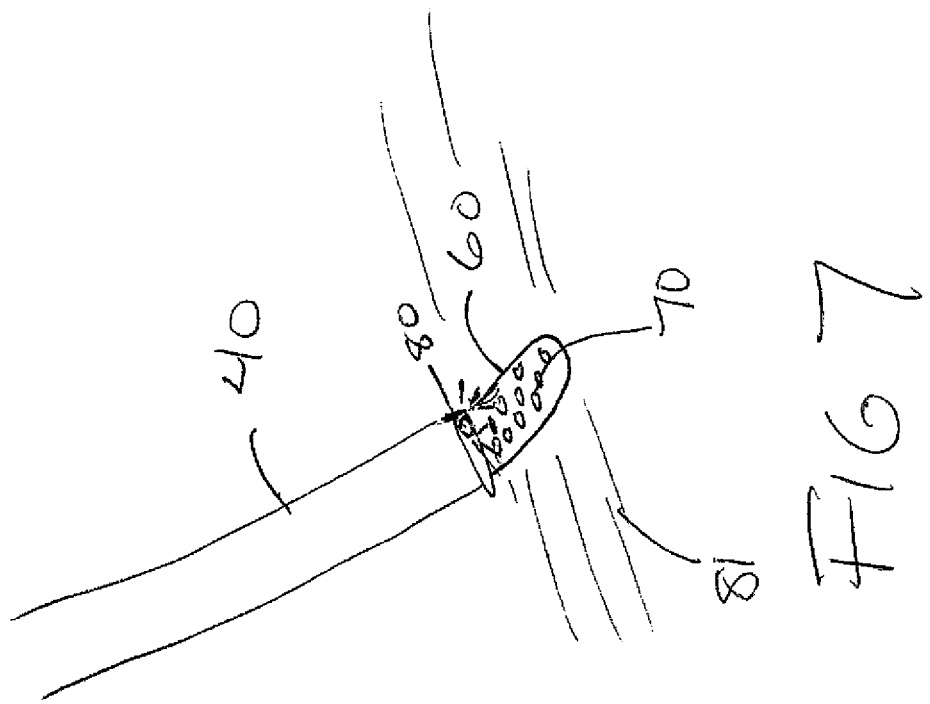

SYSTEM AND METHOD FOR DIAGNOSING AND TREATING DISEASE

CROSS REFERENCE TO RELATED APPLICATIONS

This application is a non-provisional of 61/700,350 filed Sep. 13, 2012. This application is also a continuation-in-part of U.S. patent application Ser. No. 13/529,191, filed on Jun. 21, 2012, which is a continuation-in part of U.S. patent application Ser. No. 13/438,003, filed on Apr. 3, 2012, which claims priority under 35 U.S.C. 119(e) of U.S. Provisional Application No. 61/612,575 filed on Mar. 19, 2012. U.S. patent application Ser. No. 13/529,191 also claims priority under 35 U.S.C. 119(e) of U.S. Provisional Application Ser. Nos. 61/650,401 and 61/650,429, both filed on May 22, 2012. The disclosures of all of these applications are herein incorporated by reference.

BACKGROUND OF THE INVENTION

1. Field of the Invention

The present invention relates to a system and method for diagnosing disease, such as cancer or bacterial infection. The invention relates to a method where an individual takes a high resolution photograph of a wound or diseased area of the body using a camera connected to an endoscope, or via an X-ray or MRI, sends the photograph to a computer where it is magnified and enhanced, and software in the computer then searches a database containing a library of diseases to find a match. Once a match has been found, the software can search a more specialized database pertaining to the disease that has been identified, and can send a diagnosis to a doctor or to an individual for treating the disease or infection. The entire process takes place in real time, so that the doctor can obtain the diagnosis during the procedure or while the patient is still in the office or hospital.

2. The Prior Art

Photographic databases of diseased cells and bacteria are in use today to help doctors and scientists diagnose illness and infection. In most situations, the scientist or laboratory worker places the cells on a slide under a microscope and takes a photograph of the cells under magnification. These cells can then be compared to the various photographs of similar cells in the database to help diagnose the illness. On example of this can be seen in U.S. Pat. No. 5,911,139 to Jain et al., the disclosure of which is herein incorporated by reference. Jain at al. describes a system for matching a photograph of cells taken under a microscope with photographs in a database.

U.S. Pat. No. 7,756,309 to Gholap et al., the disclosure of which is herein incorporated by reference, also describes a system for indexing and matching medical images in a database.

However, neither of these references teach a method in which in vivo injuries or illnesses can be quickly and remotely diagnosed and treated, without the use of slides and microscopes.

United States Patent Application Serial No. 2007/0015989 to Desai discusses connecting a camera of an endoscope to a computer having a database of photos to match to the images on the endoscope to assist the physician in diagnosing disease. However, Desai refers to only a single database installed on the computer, and does not allow for enhancement or enlargement of the image to allow for better diagnoses.

SUMMARY OF THE INVENTION

It is therefore an object of the invention to provide a system and method for diagnosing illness or infection in real time.

The present invention comprises a method and system for diagnosing and treating infection or disease, in which an individual takes a photograph of an infected or diseased area of a body using a high definition camera connected to a microprocessor and communication device. The camera could be incorporated into a smartphone or into a medical instrument such an endoscope, or could be an X-ray machine, MRI machine or other type of imaging apparatus. The camera or imaging apparatus is equipped to take very high resolution images that can be enlarged to a degree where individual cells and bacteria can be discerned. The image is then sent to a computer having a microprocessor equipped with image enhancing software. The software can enlarge and enhance the image to the point where individual cells, bacteria or other microscopic structures can be seen. The image is preferably enhanced up to 1000× to achieve the required degree of detail. The software can also layer photographs to enhance their resolution when enlarged. The software could also create virtual staining on the image, to enhance its resolution. The software could also be equipped to create a three-dimensional image of a body part as well.

The enhanced image is then scanned and compared to an initial database in the computer or accessible by the computer, which then categorizes the image based on the medical condition shown, for example, skin cancer, bacterial infection, etc. Additional software in the computer then searches for a database related to the category shown, and conducts a search of images in the second database that match the image obtained from the camera or imaging apparatus. The second database could be installed on the computer, or accessible over the internet.

To cut down on the amount of searching required, the user can also specify a particular type of disease or enter other pertinent data, to narrower the search to a particular group of diseases or injuries. If no match is found in the initial database, the microprocessor can then prompt the physician to enter more detailed information, such as fever or other symptoms, to help narrow down the field.

If a match is found in the second database, the microprocessor then notes the disease or bacteria corresponding to the matching photograph and communicates this to the physician by displaying the matching photographs and identification data on a display device connected the computer. The display device could be a computer monitor or could be holographic. The communication could also be verbal, via computer generated voice instructions. If an endoscope is being used, the display could also be projected onto the lens of the scope or onto glasses worn by the physician, so that the physician does not have to even look up from the scope to obtain the information. Any suitable means of displaying or conveying the information could be used.

The present invention provides an instantaneous method for diagnosing and injury, illness and infection. The present invention enhances a medical procedure, for example endoscopy, by immediately informing the physician about the type of disease located, and allows the physician to continue scanning until all diseased areas have been located and excised.

To assist in identification of the disease, a dye can be applied to the infected or diseased area prior to photographing it. Alternatively, the dye could be applied via computer enhancement of the image. In addition, a video could also be taken of the infected or diseased area. The video would show the behavior of the bacteria or microorganisms in the wound. For example, if the specific pathogen cannot be seen, the video could show the rapid deterioration of the cells, thus indicating a certain type of bacterial or viral infection. The database could also contain video recordings of similar infections for comparison as well.

In another embodiment, an attachment is added to the endoscope so that a layer of cells is trapped between the attachment and the light source of the endoscope. This creates a slide-like appearance that enhances the visual image taken by the camera. Thus, an instant slide is created, saving time and money in the diagnosis of disease.

The software connected to the microprocessor could also be equipped to notify various government and health agencies if certain types of diseases have been identified.

BRIEF DESCRIPTION OF THE DRAWINGS

Other objects and features of the present invention will become apparent from the following detailed description considered in connection with the accompanying drawings. It is to be understood, however, that the drawings are designed as an illustration only and not as a definition of the limits of the invention.

In the drawings, wherein similar reference characters denote similar elements throughout the several views:

FIG. 7 shows the device of FIG. 6 in use on a patient; and

FIG. 8 shows an alternative embodiment of the device of FIG. 6.

DETAILED DESCRIPTION OF THE PREFERRED EMBODIMENTS

Figure 1:
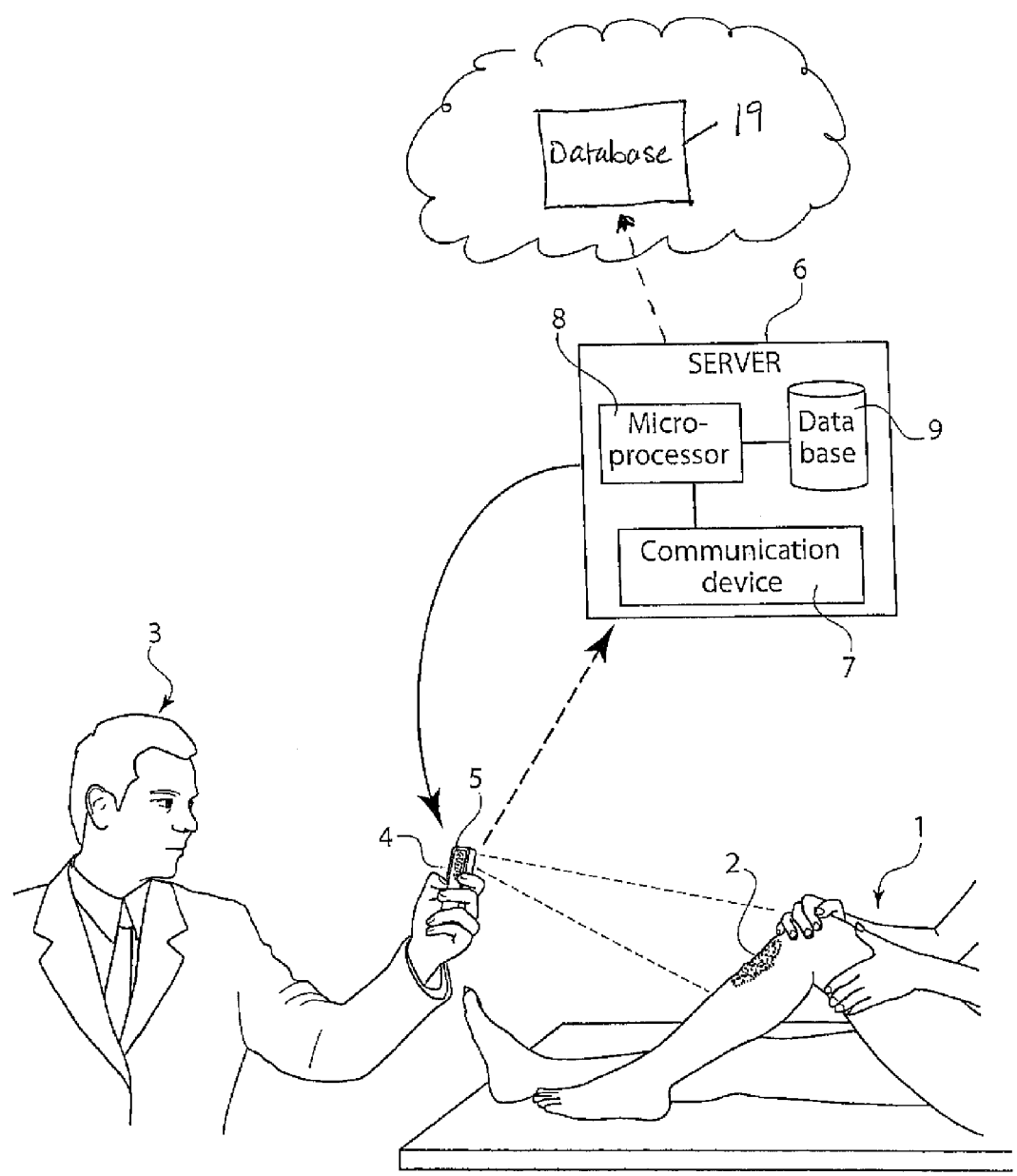
FIG. 1 shows a schematic drawing of the system according to the invention in use for treating a patient.

Referring now in detail to the drawings, FIG. 1 shows a patient 1 with an infected wound 2. An individual 3 treating patient 1 has an individual microprocessor such as a mobile smart phone 4 with a built-in camera 5. Camera 5 is adapted to take very high-resolution photographs that can be enlarged to show individual cells and/or bacteria. To treat patient 1, individual 3 takes a photograph of wound 2 using camera 5 in mobile phone 4. The camera 5 could also be connected to a hard-wired microprocessor in a clinical setting. This microprocessor could also be connected with magnification equipment such as an endoscope, which can magnify the diseased area prior to taking the photograph. The photograph is then sent by the individual via text message or email to a server 6 via having a communication device 7, such as a modem. Server 6 is equipped with a microprocessor 8, which can scan the received photograph, and using software installed on server 6, enlarge and enhance the photograph to see the individual cells and bacteria of wound 2. Microprocessor 8 then searches initial database 9, which contains photographs of many different diseases, to find a match to the photograph sent by individual 3. This search can be conducted with any suitable visual matching software, such as those discussed in U.S. Pat. Nos. 5,911,139 and 7,756,309, the disclosures of which are herein incorporated by reference. Once a match has been found, the microprocessor 8 searches database 19, which is a specialized database correlated to the identification made from database 9. If no match is found, the system notifies individual 3, and prompts individual 3 for further information about the disease being searched. Microprocessor 8 can then use this extra information to continue a search in database 9 to find the closest match, which is then used to locate the proper database 19 for conducting the second search.

If a match is made to a particular disease in database 19, the microprocessor then searches database 19 for a suitable treatment plan, which correlates with the photograph in database 19 that matches the photograph sent by individual 3. Once a treatment plan has been identified, it is sent via communication device 6 to mobile telephone 4 for use in treating patient 1.

Figure 3:
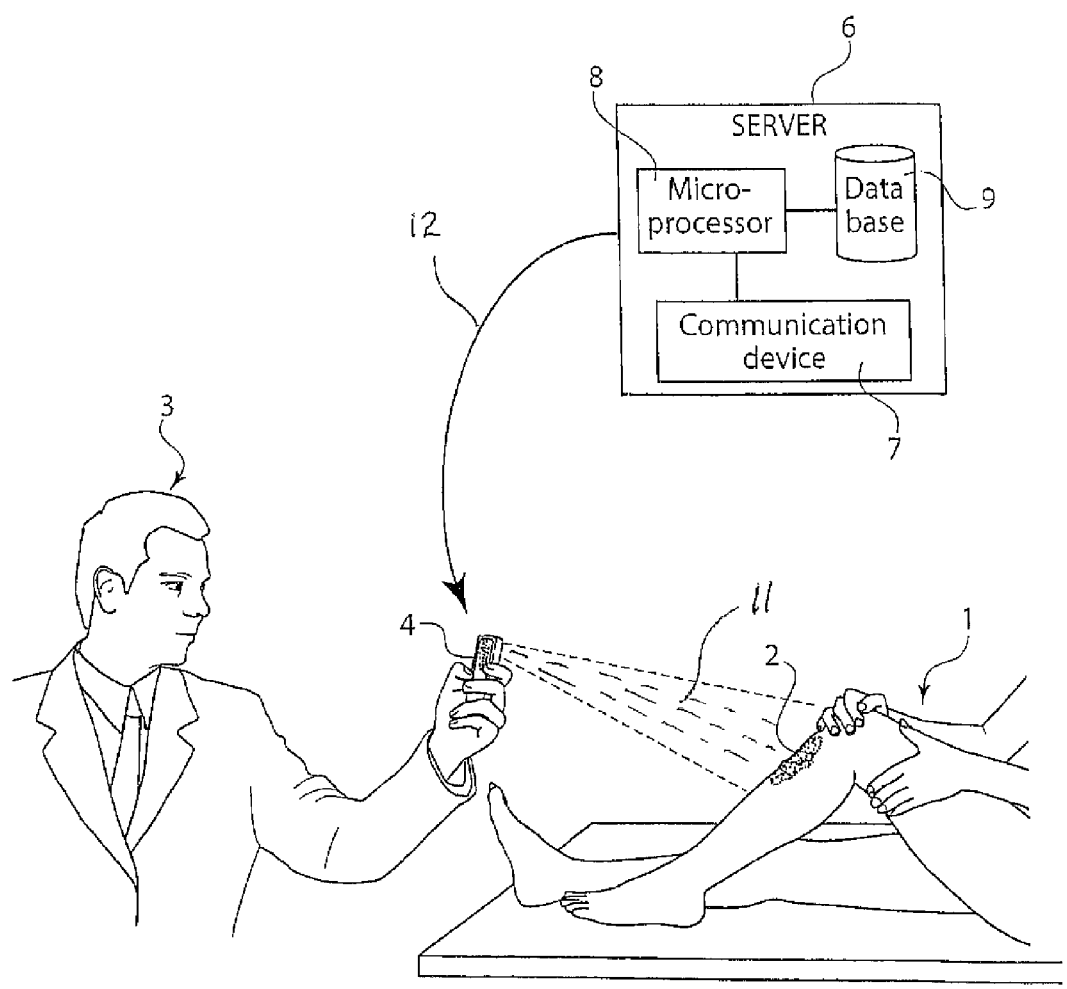
FIG. 3 shows a drawing of a treatment plan according to one embodiment of the invention.

In one embodiment, the treatment plan involves exposing the wound 2 to a wavelength of light that will kill any bacteria in wound 2. As shown in FIG. 3, microprocessor 8 sends a software application 12 to mobile phone 4, which generates such a light beam 11.

Figure 2:
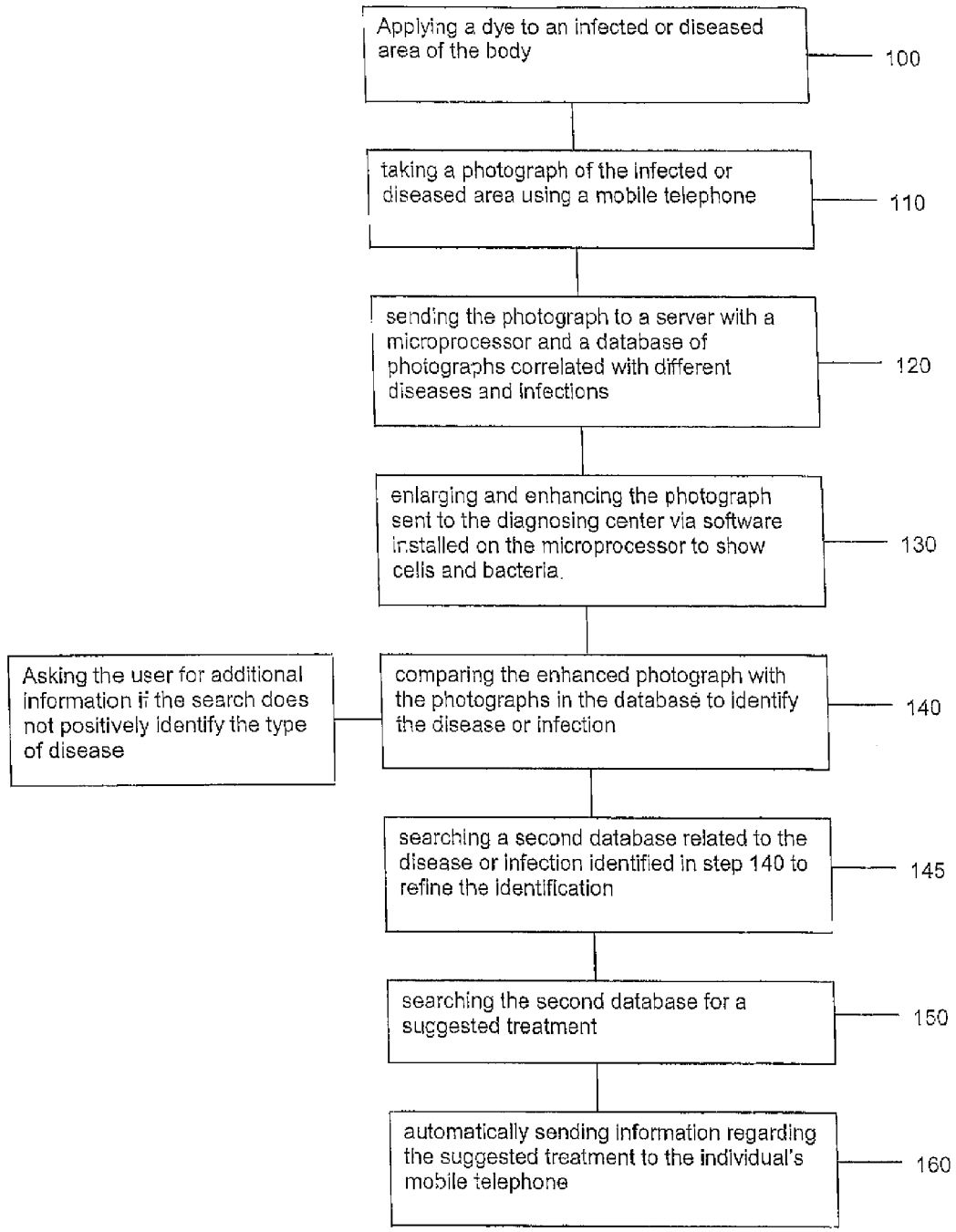
FIG. 2 shows a flow diagram of the method steps according to the invention.

FIG. 2 shows the method steps according to one embodiment of the invention. In step 100, a dye is applied to an infected or diseased area of the body, to enhance the visual resolution of the infected or diseased area. In step 110, a photograph is taken of the infected or diseased area using a smartphone having a built in camera, or using a camera connected to another type of microprocessor, such as a personal computer. Instead of or in addition to the photograph, a video showing the behavior of infected cells could also be taken.

In step 120, the photograph is sent by text message or email to a diagnosing center having a server with a microprocessor and a database of photographs correlated with different diseases and infections. In step 130, the photograph is enlarged and enhanced via software installed on the microprocessor so that individual cells or bacteria can be seen in the enhanced photograph.

In step 140, the enhanced photograph is compared with the photographs in the database to identify the disease or infection, using visual comparison software. In step 145, if a disease or infection is identified, the enhanced photograph is then compared to photographs in a second, specialized database that is specifically directed to the identified disease from step 140. If no disease can be identified in step 140, the individual can be asked to provide additional information about the disease to be searched in step 146. This information is then used to look at first database again in an attempt to identify the disease or infection. Once the disease or infection has been identified, the microprocessor searches the second database for a suggested treatment in step 150. In step 160, the microprocessor automatically sends information regarding the suggested treatment to the individual's mobile phone or microprocessor. The treatment information could also be displayed holographically. For example, if the camera is connected to an endoscope, the treatment could be projected onto the lens of the endoscope so that the physician would not need to look up from the procedure to obtain the necessary information.

Figure 4:
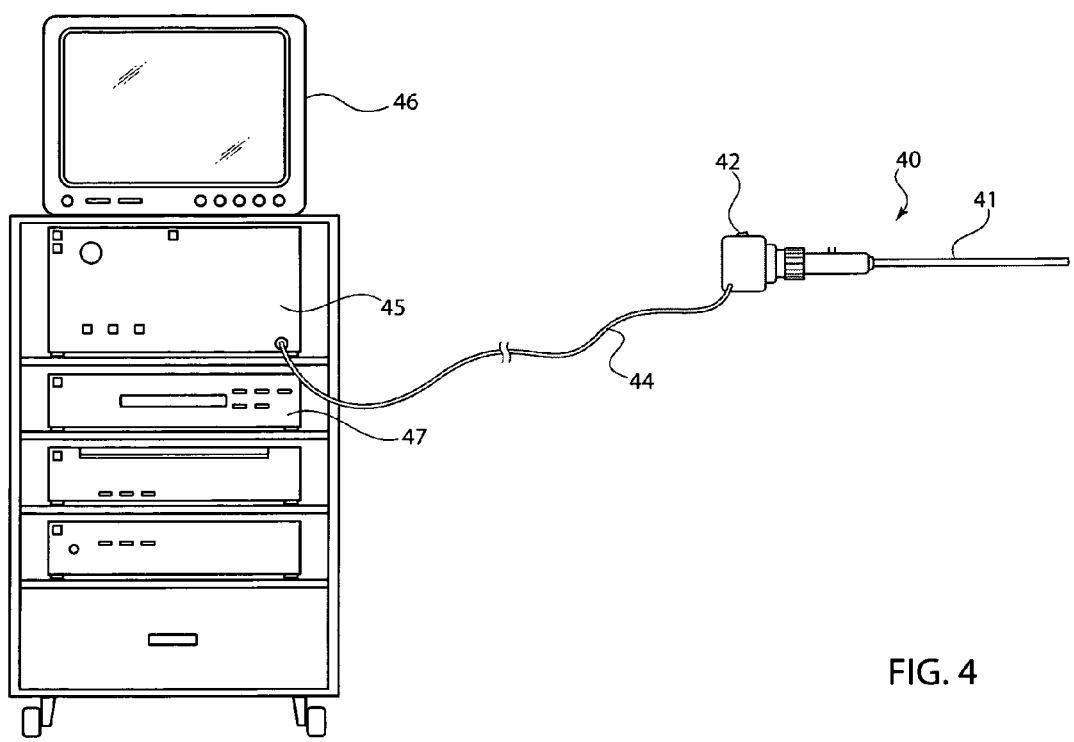
FIG. 4 shows the system according to the invention used with an endoscope.
Figure 5:
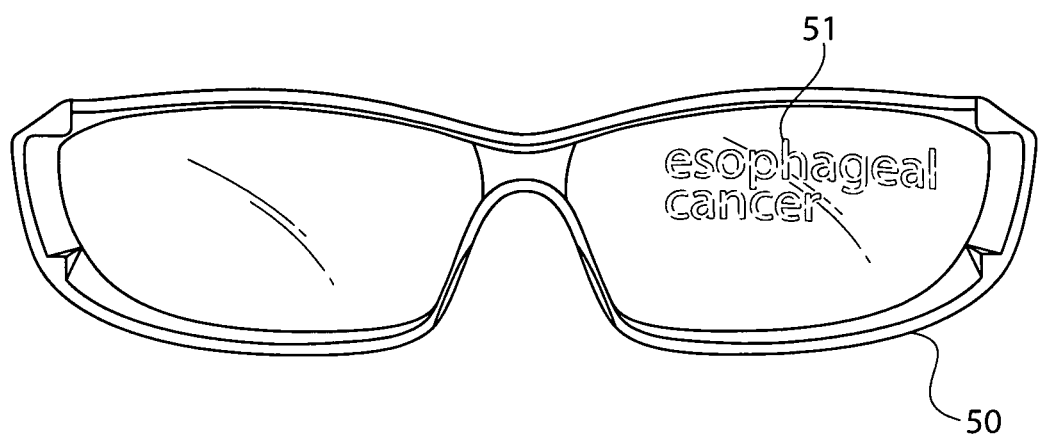
FIG. 5 shows a diagnosis being displayed holographically.

FIG. 4 shows how the invention would operate using a camera connected to an endoscope. Endoscope 40 has a shaft 41 connected to a camera 43, which can record video and still images seen through shaft 41. The video and still images are transmitted to microprocessor 45 via cable 44. The video and still images can also be displayed on display screen 46. Microprocessor 45 is connected to a communication device 47, which can be a modem. As with the embodiment in FIG. 1, the images obtained by camera 1 can be compared to an initial database stored inside a database connected to microprocessor 45, and if a match is found, then sent to a second database, accessible over the internet, for a more refined diagnosis. Once the final diagnosis has been made, the diagnosis and possible treatments are sent back to the physician, and can be displayed on display 46, or can be communicated in another manner, such as by voice or holographically onto an eyepiece or lenses 50 worn by the physician, such as shown in FIG. 5. FIG. 5 shows a holographic message 51 being projected onto glasses 50, which can be worn by the physician during the procedure, so that the physician does not have to look away from the procedure to receive the diagnosis. The holographic message 51 could also be projected onto a lens of a microscope, or the endoscope, or even onto a wall or other surface.

Figure 6:
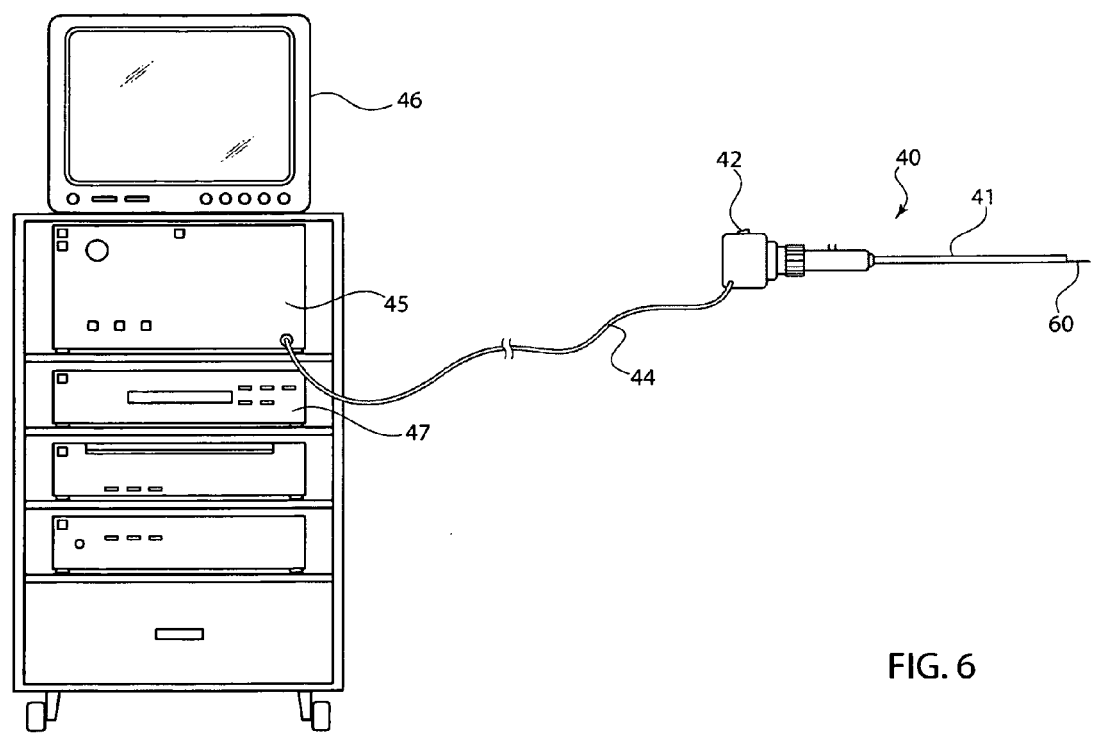
FIG. 6 shows an alternative embodiment of the device of FIG. 4 with an extension.

As shown in FIGS. 6 and 7, endoscope 40 can have an extension 60 attached to its distal end. In use, extension 60 can be inserted into the tissue of a patient so that a layer of cells 70 lies on top of the top surface of the extension. This layer can then be illuminated, either from behind, if the extension is translucent (as shown in FIG. 8), or from the front, by the light source 80 of endoscope 40 (as shown in FIG. 7). The layer can be the thickness of a single layer of cells. Thus, the camera 43 takes an image that is essentially a prepared slide for sending to microprocessor 45. Thus, the cells of the tissue being examined are more visible and the diagnosis can be made more easily. This procedure also saves the time and expense required in preparation of slides in a laboratory.

Accordingly, while only a few embodiments of the present invention have been shown and described, it is obvious that many changes and modifications may be made thereunto without departing from the spirit and scope of the invention.

What is claimed is:

1. A method for diagnosing and treating infection or disease, comprising:
    inserting an endoscope into a patient's body, the endoscope having a light source and an extension on a distal end thereof;
    placing the extension underneath a layer of tissue in the patient;
    illuminating the extension with the light source from underneath the top surface of the extension, so that light from the light source shines through the layer of tissue; and
    taking a photograph of said illuminated layer of tissue using a camera connected to a first microprocessor, the camera being connected to the endoscope;
    sending the photograph via the first microprocessor to a server with a second microprocessor and a first database of photographs correlated with different diseases and infections, the photographs showing individual diseased cells or bacteria;
    enlarging and enhancing the photograph sent to the server via software so that individual cells or bacteria can be seen in the enhanced photograph;
    comparing the enhanced photograph with the photographs in the first database to identify the disease or infection, the step of comparing being undertaken by the second microprocessor using visual comparison software;
    upon identifying the disease or infection, searching for a second database that is correlated with the identified disease or infection, and once said second database is located, comparing the photograph with photographs in the second database to further identify the disease or infection;
    once the disease or infection has been identified via the second database, the second microprocessor searching the second database for a suggested treatment; and
    automatically sending information regarding the suggested treatment via the second microprocessor to the first microprocessor.

2. The method according to claim 1, further comprising the step of applying a dye to the layer of tissue prior to the step of taking a photograph.

3. The method according to claim 1, further comprising the step of taking a video of the layer of tissue and sending the video to the diagnosing center.

4. The method according to claim 1, wherein the layer of tissue contains a single layer of cells.

5. The method according to claim 1, further comprising the step of displaying the suggested treatment holographically.

6. The method according to claim 1, further comprising the step of prompting the individual for information regarding a suspected disease or infection prior to or after the step of comparing the enhanced photograph with photographs in the first database.

7. The method according to claim 1, wherein the photograph is enlarged by a factor of 1000.

8. A system for diagnosing and treating infection and disease comprising:
    an endoscope having a light source for illuminating tissue, and an extension connected to a distal end of the endoscope, the extension being configured to insert within tissue of a patient such that a layer of tissue covers a top surface of the extension and can be seen through the endoscope wherein the light source is adapted to illuminate the extension from underneath the top surface of the extension, so that light from the light source shines through the layer of tissue, and;
    a camera connected to the endoscope and to a microprocessor, the camera adapted to take photographs of images of the illuminated tissue layer seen through the endoscope and send said photographs to the microprocessor;
    a server having a microprocessor and a searchable database, the database containing a collection of photographs of diseased cells and bacteria,
    a communication system connected to the server, said communication system being adapted to receive communications containing photographs from an outside source and send the communications to the server,
    wherein the microprocessor is programmed with software that analyzes a photograph in a received communication, enhances and enlarges the photograph, compares the photograph to the photographs in the database to find a match, and when a match is found, communicates with an outside database correlated with the match to further search the outside database for additional information to identify a disease in the photograph, and then searches for a treatment plan for a disease associated with the match and sends the treatment plan via the communication system to a microprocessor of the outside source.

9. The system according to claim 8, wherein the extension is translucent.

* * * * *